United States Patent [19]

Seppi

[11] 4,149,081
[45] Apr. 10, 1979

[54] REMOVAL OF SPECTRAL ARTIFACTS AND UTILIZATION OF SPECTRAL EFFECTS IN COMPUTERIZED TOMOGRAPHY

[75] Inventor: Edward J. Seppi, Mountain View, Calif.

[73] Assignee: Varian Associates, Inc., Palo Alto, Calif.

[21] Appl. No.: 745,709

[22] Filed: Nov. 29, 1976

[51] Int. Cl.² .................. A61B 6/02; G01N 23/08
[52] U.S. Cl. .......................... 250/445 T; 364/414; 364/515
[58] Field of Search ............... 250/445 T; 235/151.3

[56] References Cited

U.S. PATENT DOCUMENTS 4,029,963   6/1977   Alvarez et al. .............. 250/445 T

OTHER PUBLICATIONS

*American Institute of Physics Handbook*, Second Edition, McGraw-Hill, New York, 1963, pp. 8-81.
Zaklad, Haim, "Computerized Multiple X-Rays Give a New View of the Body's Interior," *Electronics*, Oct. 14, 1976, pp. 89-94.
McCullough et al., "An Evaluation of the Quantitive and Radiation Features of a Scanning X-Ray Transverse Axial Tomograph: The EMI Scanner," *Radiology*, 111:709-716, Jun. 1974.
Alvarez et al., "Utilization of Simple Energy Spectrum Measurements in X-Ray Computerized Tomography," appearing at MB1-1 of the Digest of Technical Papers presented at the Topical Meeting on *Image Processing for 2-D and 3-D Reconstruction from Projections*, held at Stanford University, Palo Alto California, Aug. 4-7, 1975.
Alvarez, Robert E., *Extraction of Energy Dependent Information in Radiography*, Stanford University Doctoral Dissertation, Jul. 1976.
Alvarez et al., "Noise and Dose in Energy Dependent Computerized Tomography," *Proceedings of the Society of Photo-optical Instrumentation Engineers*, vol. 96, pp. 131-137, Sep. 16-19, 1976, Washington, D.C.
Alvarez et al., "Non-linearities in Projection Reconstruction," *Optical Society of America Annual Meeting Program*, Oct. 18-22 1976, Tucson, Arizona.
Macovski et al., "Correction for Spectral Shift Artifacts in X-Ray Computerized Tomography," appearing at MB1-5 of the Digest of Technical Papers presented at the Topical Meeting on *Image Processing for 2-D and 3-D reconstruction from Projections* held at Stanford University, Palo Alto, California, Aug. 4-7, 1975.
Macovski et al., "Energy Dependent Reconstruction in X-Ray Computerized Tomography," *Computers in Biology and Medicine*, vol. 6, No. 4, Oct. 1976, pp. 325-336.

*Primary Examiner*—Alfred E. Smith
*Assistant Examiner*—T. N. Grigsby
*Attorney, Agent, or Firm*—Stanley Z. Cole; Gerald M. Fisher; Edward J. Radlo

[57] ABSTRACT

In an instrument for reconstructing computerized tomograms utilizing penetrating radiation, typically x or gamma radiation, an apparatus and technique are disclosed for removing spectral artifacts and utilizing spectral effects to create output pictures which represent facsimilies of the distribution of molecules according to atomic number and electron density within the object being pictured. Combinations of these pictorial representations are also obtained. Reconstruction errors caused by panchromaticity in the radiation source are avoided. Attenuation within the object by means of photoelectric absorption, Compton scattering and Rayleigh scattering are isolated and analyzed separately. Techniques are disclosed for treating source beams which are arbitrarily thin or of a finite thickness. Measurements at two source spectra are performed either by means of different peak energy settings of the source, the use of a source input filter, or the utilization of detectors of different efficiencies or different response ranges, or a combination of any of the above. A statistical error analysis of the output picture is provided as a function of the statistical error in each of the two sets of measurements. A computerized fit using the least squares technique is made to establish parameters yielding analytical expressions for the various attenuation cross-sections. A calibration technique is disclosed which utilizes empirical measurements. A method for optimizing the measurement technique is disclosed. Finally, an analysis of the error in the waterbag technique is provided.

17 Claims, 5 Drawing Figures

REMOVAL OF SPECTRAL ARTIFACTS AND UTILIZATION OF SPECTRAL EFFECTS IN COMPUTERIZED TOMOGRAPHY

BACKGROUND OF THE INVENTION

1. Field of the Invention

This invention relates to an apparatus and method for reconstructing two-dimensional pictures of object slices within a human or other body by means of passing penetrating radiation, typically X-radiation or gamma radiation, through the plane of the body from a plurality of angles. The field is commonly known as computerized tomography or transverse axial tomography.

2. Description of the Prior Art

Figure 1:
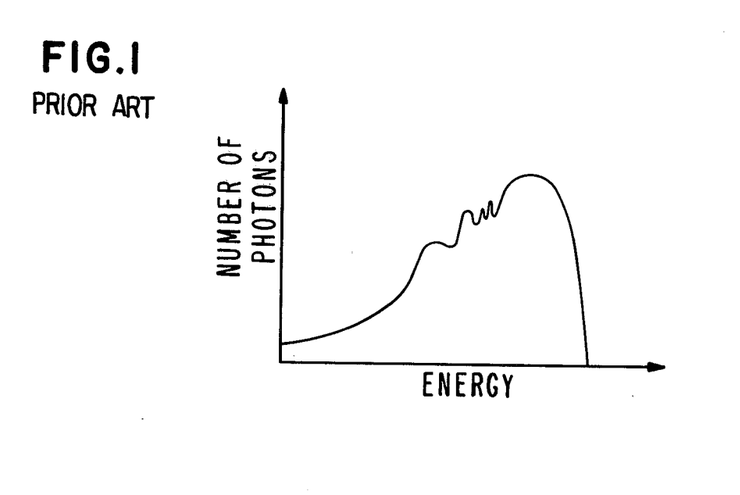
FIG. 1 is a graph of number of photons vs. energy in a typical X-ray beam useful for medical diagnostic purposes in computerized tomography.

In present applications of X-ray computerized tomography, X-ray source energies which are useful for medical diagnosis are inherently panchromatic, i.e. the incident X-ray spectrum is not all focused at one energy, but rather is in a spectral shape representing a whole host of different energies. FIG. 1. This has unfortunate ramifications for the quality of the output pictures thus obtained because all of the reconstruction methods in current use, regardless of source-detector geometry, proceed on the assumption that the incident X-ray beam is monoenergetic. Thus it has been recognized that it would be desirable to remove from the output displays those artifacts caused by the panchromatic nature of the incident beam. An early approach to the solution of the problem revolved around the use of a waterbag. The problem is discussed in McCullough et al., "An Evaluation of the Quantitative and Radiation Features of a Scanning X-Ray Transverse Axial Tomograph: The EMI Scanner," *Radiology* 111:709–716, June, 1974.

A previous sketchy approach to this problem can be found in a paper entitled "Utilization of Simple Energy Spectrum Measurements in X-ray Computerized Tomography", by Robert E. Alvarez and Albert Macovski, appearing at MB1-1 in the Technical Digest for the Conference, "Image Processing for 2-D and 3 -D Reconstruction from Projections: Theory and Practice in Medicine and the Physical Sciences", August 4–7, 1975, Stanford University, Palo Alto, California. This publication suffers from several infirmities. First, there is no mention of any technique for treatment of the physical phenomenon known as Rayleigh scattering. Second, there is no mention of how detectors may be utilized to obtain different spectral information. Third, there is no analysis of the errors which are generated using the technique described. Fourth, in description of the test which was performed, FIG. 1 shows output sketches of a photoelectric phenomenon and a Compton scattering phenomenon, with no relation of these drawings to the atomic number of the molecules in the object under study or the electron density of same. Fifth, the calibration and generation of output pictures was achieved using computer simulated data, not actual data actually measured by a tomographic scanner.

OBJECTS OF THE INVENTION

It is therefore a primary object of the present invention to isolate the photoelectric absorption, Compton scatter, and Rayleigh scatter components of attenuation in computerized tomography and to obtain improved generalized pictorial representations of the attenuations due to these phenomena.

It is a further object of the present invention to remove spectral artifacts from computerized tonograms in an improved fashion.

It is a further object of the present invention to obtain accurate analytical expressions for radiation attenuation cross-sections due to each of photoelectric absorption, Compton scatter and Rayleigh scatter, which are used in energy-dependent tomography.

It is a further object of the present invention to obtain from the same object slice under investigation an improved pictorial representation of the atomic number of the molecules in the object slice and the electron density distribution of said molecules.

It is a further object of the present invention to obtain in tomography improved pictorial representations of combinations of the atomic number distribution and electron density distribution within the object under study.

It is a further object of the present invention to utilize all the energy information contained in beams of arbitrary thinness or of finite thickness in X-ray tomography.

It is a further object of the present invention to demonstrate how one can obtain optimal spectral information in computerized tomography by means of using detectors of different efficiencies or response ranges, source input filters, or different peak energy settings of the X-ray or gamma ray source, or any combination of the above.

It is a further object of the present invention to provide a statistical error analysis of the error in any of the output pictures obtained by the present invention as a function of the statistical errors in each of the sets of measurements which are taken by the detectors as a means to provide such output pictures.

It is another object of the present invention to disclose a calibration system for energy-dependent tomographic apparatus which is based upon actual measurements taken by the apparatus.

It is another object of the present invention to isolate and utilize spectral information in tomographic apparatus for a nonrecording convolution reconstruction algorithm used with diverging fan beam geometry employed in the apparatus.

It is another object of the present invention to display an improved computerized tomographic facsimile of an object under study in such a way that compensating decreases in electron density do not mask out increases in atomic charge.

It is another object of the present invention to remove spectral artifacts from computed tomograms in an improved fashion whilst exposing the pictured object to a much lower dose of radiation than in systems using waterbags to attenuate said artifacts.

SUMMARY OF INVENTION

Briefly and in accordance with the above objects, the present invention is concerned with apparatus and methods for constructing two dimensional pictures of an object slice by means of detection of penetrating radiation not attenuated by the object slice during an analysis of said object slice in computerized tomography.

Present techniques for reconstructing two dimensional pictures in X-ray tomography make the assumption that the source X-ray beam is monoenergetic. In reality, X-ray sources which are useful for medical diagnosis are by their very nature panchromatic, i.e., are represented by a spectrum of energy, as illustrated in FIG. 1. This faulty assumption creates spectrum artifacts in the resulting output pictures of the prior art. The present invention overcomes this problem by fully taking into account the entire incident spectrum of energy. At the same time, the invention separates out the attenuation components due to photoelectric absorption, Compton scattering and Rayleigh scattering. The present invention produces output pictures of the atomic charge distribution within the object slice being investigated and of the electron density distribution within said object slice, or any combination of these two variables.

A computer program takes as its input empirical values of the various attenuation cross-sections present, and by means of the least squares technique, gives parameters which enable one to set up analytical expressions for the three various attenuation cross-sections present in any object under study. A technique is disclosed by means of which the three analytical expressions are combined with expressions for detector efficiency and input spectra to represent a set of two equations. It is then shown that if one takes two sets of measurements, these two sets of equations can be solved, yielding output pictures of atomic charge distribution and electron density distribution, or any combination thereof, for either a thick or thin beam case of the object under study. These two sets of measurements may be taken by means of using different peak energy settings of the x-ray source, using detectors with different efficiencies or energy response ranges, by using an input source filter, or by any combination of the above. A technique is disclosed for optimizing the thickness of such a source filter. A similar technique can be used to optimize source spectra, detector sensitivity, or combinations thereof. In practice, it is preferable to use two sets of detectors to minimize drift and respiration artifacts. The machine is also calibrated empirically during the solution of the sets of equations.

The techniques of the invention are independent of the reconstruction algorithm used, and independent of the source-detector geometry used.

A statistical error analysis is then provided which shows the statistical error present in the output pictorial representations as a function of statistical errors in the two sets of measurements.

It is additionally shown that the waterbag technique commonly used in tomography is sysceptible to new artifacts. When combined with the error analysis of photon artifacts presented in the specification, tables giving differences in effective charges for various anatomical organs of the human body show which organs can be distinguished from each other using the present invention.

The techniques of the invention may be collectively termed "spectrally independent transverse axial tomography" (SITAT).

BRIEF DESCRIPTION OF THE DRAWINGS

These and other more detailed and specific objects and features of the instant invention are more fully disclosed in the following specification, reference being had to the accompanying drawings in which.

I. Spectrum Problem

In this section of the disclosure we present a technique by which the spatial distribution of the electron density (number of electrons per $cm^3$) and the effective Z (atomic charge) of material within a thin slab can be determined using an image reconstruction technique which takes advantage of the spectral distribution of the emission spectrum from a standard medical X-ray tube and the spectral dependence of associated X-ray detectors. The usual techniques used in transverse axial tomography for image reconstruction assume that the initial line integral data used in the reconstruction algorithm is the result of measurement using a mono-energetic photon beam, an unrealistic assumption for X-ray beams in the diagnostic range. FIG. 1. For our purposes, these reconstruction techniques solve the following problem. Given the line integral of the attenuation along lines in all directions drawn through all points in a plane, the reconstruction algorithm calculates the X-ray attenuation density distribution at all points within the plane. One formulation of the solution to this problem is described in U.S. patent application Ser. No. 643,896 to Pavkovich, filed Dec. 23, 1975, and in U.S. patent application Ser. No. 643,894 to Pavkovich and Nunan, filed Dec. 23, 1975, and assigned to the same assignee as the present invention. If the line integral of the attenuation density at photon energy E for a line ($\theta$, $\beta$), is represented by H ($\theta,\beta E$) and the attenuation density at the point R for energy E is represented by Q (R, E) then, $$Q(\vec{R},E) = -\frac{1}{\pi} \int_0^\infty dr_1 \frac{1}{r_1} \frac{d}{dr_1} \left( \frac{1}{2\pi} \int_0^{2\pi} d\alpha_1 H(\theta,\beta,E) \right) \quad (1)$$

and $$H(\theta,\beta,E) = \int_{\text{line}} Q(\vec{R},E) dl \quad (2)$$

As was pointed out above, in previous formulations of this technique it has been assumed that the function H is known at some particular energy E. In a measurement using a monochromatic X-ray beam the function H can be determined from Beer's Law since in this case the line integral H is simply given by the logarithm of the transmission of the beam through the object under study along lines passing through each point in the plane at all angles. The problem is more difficult if the X-ray beam used for the measurement is not monochromatic. If we represent the spectral dependence of the incident X-ray beam by $\Phi(E)$ where $\Phi$ dE is the number of photons per square cm second in the range between E and E+dE and if we have a detector of the efficiency $\epsilon(E)$ at energy E, the detected intensity after passing through a sample with line integral H is given by $$I_1 = \int \Phi_1(E)\epsilon(E)e^{-H}dE \quad (3)$$

and $$I_{01} = \int \Phi_1(E)\epsilon(E)dE \quad (4)$$

is the intensity measured with no object in the path of the beam.

We now see that in equation 3 and 4 if $\phi(E)$ is a Dirac delta function in energy, the determination of H is simple and becomes $$H = \ln I/I_o \quad (5)$$

However, if $\Phi_1$ is not a delta function, the solution of equations 3 and 4 for H becomes more difficult. McCullough et al., supra, discussed some solutions which have been proposed to solve this problem. One such solution is the use of a waterbag. This technique will be discussed in section VII. The use of a waterbag takes advantage of the fact that human tissue and water have essentially equivalent X-ray attenuation densities with the result that it is possible to assign an effective energy to the broad spectrum X-ray beam and to treat the transverse axial tomography problem of image reconstruction as though the measurements were made with the monochromatic X-ray beam of the assigned effective X-ray energy.

A superior technique to the solution of this problem, described here, takes advantage of known functional dependence of X-ray scattering attenuation cross-sections on the incident X-ray energy. In the X-ray energy region of interest in computerized tomography, the elemental X-ray cross-sections for attenuation of X-rays from an X-ray beam are the result of Compton scattering, Rayleigh scattering, and photo-electric absorption. The functional dependencies of these cross sections are known and for our purposes depend only on the energy of the incident photon and the elemental charge. Therefore, given a known X-ray beam spectrum, detector efficiency curve, and the density and chemical composition of an object, the transmission ratio $I/I_o$ given by equations 3 and 4 cam be theoretically calculated. (There are some small coherent scattering effects which depend on molecular and solid state structure which have been neglected.) For chemical compounds the attenuation is simply the result of the sum of the attenuations due to each of the elemental constituents of the material. Although the calculation of X-ray attenuation cross-sections from basic physics formulas is complicated it is possible to fit these cross-sections with the following relatively simple functional form.

$$\sigma_c \alpha Z_e \sigma(E), \sigma_a \alpha Z^{4.5}/E^3, \sigma_R \alpha \quad (6)$$

a linear combination of $\sigma_a$ and $\sigma_c$
where:
Z is the effective charge,
$_e\sigma(E)$ is the single electron Compton cross-section at energy E,
$\sigma_c$ is the attenuation cross-section due to Compton scatter,
$\sigma_a$ is the attenuation cross-section due to photoelectric absorption, and
$\sigma_R$ is the total attenuation cross-section. On this basis we assume that the X-ray attenuation density can be written in the following functional form.

$$Q(\vec{R},E) = G_c(E) \cdot q_c(\vec{R}) + G_a(E) \cdot q_a(\vec{R}) \quad (7)$$

The functions $G_a$ and $G_c$ depend only on the energy and are given to first order by the relationships $$G_a(E) \sim 1/E^3; \quad G_c(E) \sim {}_e\sigma(E) \quad (8)$$

The functions $q_a$ and $q_c$ are functions of the position $\vec{R}$ in the object, and are the attenuations due to photoelectric absorption and Compton scatter, respectively. They depend on the effective Z of the material through which the X-rays are passing, and also upon its electron density at each point $\vec{R}$. These functions are given to first order by the following expressions.

$$q_a(\vec{R}) \simeq Z(\vec{R})^{4.5} \rho(\vec{R}); \quad q_c \simeq Z(\vec{R}) \rho(\vec{R}) \quad (9)$$

where $\rho(\vec{R})$ is the number of atoms per unit volume at the position $(\vec{R})$.

In a later section we will give results of a cross-section fitting program which uses more complicated functional dependencies for equations 8 and 9, and can be used to describe the X-ray attenuation density for X-ray energies up to 150 kV and for atomic numers up to an effective Z of about twenty to within a few tenths of a percent accuracy.

We now define $h_c$ and $h_a$ as the line integrals $$h_c = \int q_c dl \quad h_a = \int q_a dl \quad (10)$$

Placing equation 7 into equation 2 and using equation 10 gives $$I_1/I_{01} = \int \Phi_1(E)\epsilon(E)e^{-(G_a h_a G_c h_c)} dE / \int \Phi_1(E)\epsilon(E)dE \quad (11)$$

for the ratio of equations 3 and 4.

If one now performs a measurement with a different incident flux $\Phi_2(E)$ one obtains the expression $$I_2/I_{02} = \int \Phi_2(E)\epsilon(E)e^{-(G_a h_a + G_c h_c)} dE / \int \Phi_2(E)\epsilon(E)dE \quad (12)$$

where $I_2/I_{02}$ is the ratio of the detected intensity after passing through the sample to the intensity with no sample in the beam using the spectrum $\Phi_2$. In practice one can obtain a different X-ray spectrum $\Phi_2$ either by (1) changing the peak energy setting of the X-ray power supply, by (2) inserting a suitable filter into the X-ray beam, or by (3) changing the efficiency $\epsilon(E)$ of the detector or using detectors sensitive over different energy ranges, such as a high energy range and a low energy range. Out of these possible approaches, the latter is preferable because it is the only approach in which all measurements for the spectrally independent reconstruction are taken at once. This means that drift of the detectors and other circuitry is minimized, and respiration artifacts, i.e., those called by the patient's breathing, are curtailed. It is also possible to use optimized combinations of these techniques. The patient is not exposed to less radiation, however. It is shown later than an approximately equivalent radiation does must be applied to achieve results equivalent to those generated by the other methods.

Figure 2A:
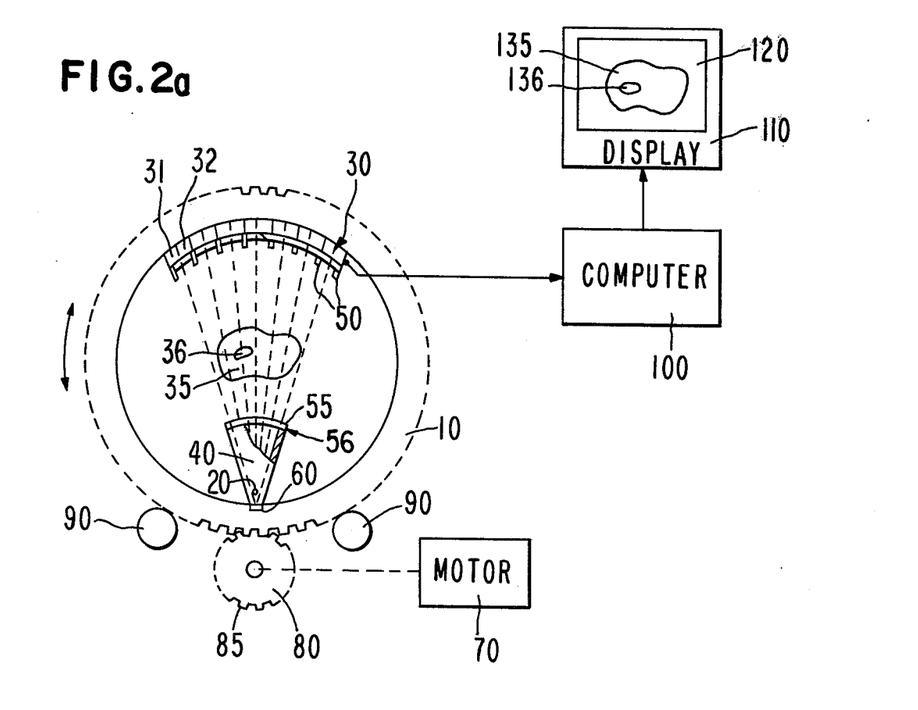
FIG. 2a is a partial diagrammatic plane view and a partial block diagram of a tomographic instrument employing the present invention.

The three embodiments are illustrated in FIG. 2a, which is a partial diagrammatic plane view and a partial block diagram of a tomographic instrument employing the present invention. Source 20 and detector array 30 are fixedly mounted on gantry 10 which rotates circularly in a plane containing the planar cross-section of object slice 35 which it is desired to depict. For example, a physician may wish to view a facsimile of tumor 36 within a human body. Motor 70 drives drive gear 80 which energizes gantry 10 by means of teeth 85 and 86. Rollers 90 keep gantry 10 aligned. Source 20 is a source of penetrating radiation such as X-radiation or gamma radiation. Collimator 40, which is comprised of a heavy substance such as lead, serves to collimate the radiation beam towards the object slice and detector array, and serves to protect the operator and patient from spurious radiation. FIG. 2a shows the beam shaped into a thin fan shape, which is a preferred shape for human diagnosis. The beam may be arbitrarily thin (up to a few millimeters thick) and fan across an angle from arbitrary smallness up to 180°, preferably about 35°. It is helpful if the distribution of photons is substantially uniform across the thickness and breadth of the beam. Those photons which are not attenuated by object 35 are detected by detectors 30, which may be a continuous arcuately shaped detector, or a set of discrete detectors, typically numbering about 300. The detectors may be scintillators/photomultipliers, solid state devices, or chambers filled with a gas such as xenon or krypton which is ionized by the incoming radiation producing signals which are then counted. In any event, at a plurality of angular positions of the source/detector array about object slice 35, signals corresponding to non-attenuated radiation are fed into computer 100, which is preferably analog when detector 30 is continuous and digiral when detector array 30 comprises a discrete set of detectors. In the latter case, collimators 50, which are comprised of a heavy material such as lead, provide shielding between adjacent detectors, thus preventing cross-talk and other interference. At this point, it must be stressed that the particular geometry shown is merely illustrative of the invention, and any other type of geometry, such as parallel pencil beams with translational as well as rotational movement, may be employed.

Upon receiving the measured data from detector(s) 30, computer 100 processes the data using the programs described herein as well as conventional reconstruction programs, and produces output data representative of two separate representations of object slice 35, each of which is free from spectral artifacts, as described herein. These output data are then transmitted to display device 110 where they are portrayed, either sequentially or simultaneously. Display 110 is any device capable of graphically portraying three-dimensional information, e.g., an electrostatic printer programmed to show contours, or a cathode ray tube 120 where differences in amplitude (here attenuation densities) are shown as different shades of grey or different colors. FIG. 2a shows the case where the two output pictures are displayed sequentially on CRT 120. In each case, FIG. 135, corresponding to object slice 35, and reconstructed tumor 136, corresponding to tumor 36, are clearly shown. The significance of the two pictures is described elsewhere in this specification.

All three embodiments of the invention are shown in FIG. 2a, as indeed all three can exist simultaneously on the same machine. The first embodiment, it will be recalled, entails changing the source energy distribution so that two successive scans of the object are taken at two different energy spectra. This may be accomplished by means of, for example, dial 60, for changing the peak energy setting, and hence the energy distribution itself, by means of changing the voltage in the source power supply. Dial 60 may have a plurality of settings; in fact, where it is continuous, it may have an arbitrarily large number of settings.

The second embodiment entails the adjustment of the energy spectrum between two separate scans by means of a filter 55 which is affixed between source 20 and object slice 35. FIG. 2a shows filter 55 fixedly mounted on collimator 40. Filter 55 is comprised of a material, such as Lucite (TM), copper, or tungsten, which allows some of the radiation to pass through while attenuating some of the radiation. A technique for calculating an optimal thickness for the filter is described elsewhere in the specification. Knob 56 is attached to filter 55 to provide for selectively changing the thickness of the filter or replacing one filter with another of different atomic number.

The first two embodiments just described may be effectuated with conventional detectors. For the third embodiment, however, it is necessary that the detector(s) be capable of simultaneously and separately recording photons at different energy levels. For example, FIG. 2a shows each detector 30 broken into a low energy sub-detector 31 and a high energy sub-detector 32, each of which is tuned to be responsive above or below a predetermined cutoff energy. Data from each set of sub-detectors is simultaneously fed into computer 100 which then processes the data into two output pictures as described herein.

Figure 2B:
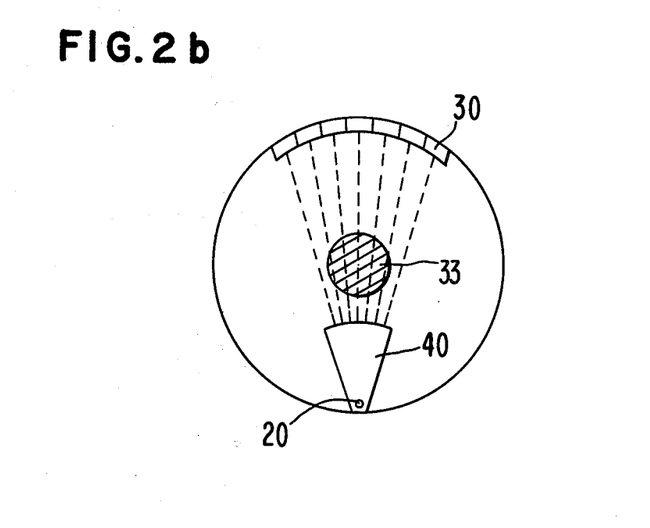
FIG. 2b is a diagrammatic plane view of a tomographic instrument employing the present invention with a test object situated therein.
Figure 2C:
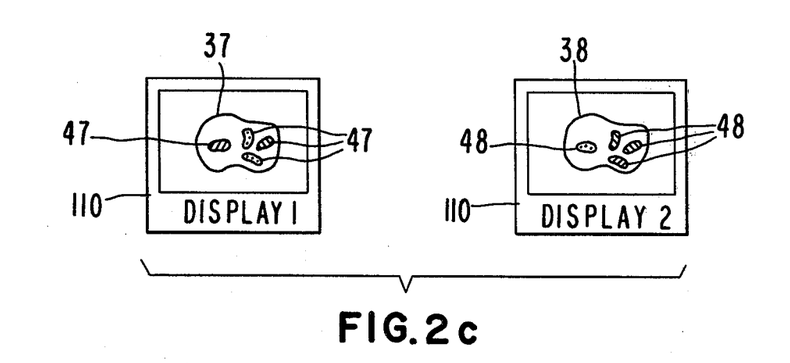
FIG. 2c is an illustration of the output of a tomographic instrument employing the present invention wherein two separate output facsimiles are displayed.

FIG. 2c illustrates these two output pictures. DISPLAY 1 and DISPLAY 2 each display object 35, as 37 and 38, respectively. These two displays may be displayed either simultaneously or sequentially upon output display device 110 as described herein. The various organs or sub-objects within object 35 are portrayed separately by the two displays as 47 and 48, respectively.

FIG. 2b illustrates the apparatus of FIG. 2a but with a test object 33 having known attenuation characteristics inserted in lieu of object 35. The test object may be, e.g., a cross-section of an aluminum cylinder.

Note that in equations 11 and 12, by definition the $G_a$ and $G_c$ depend only on the energy of the incident photons and that $h_a$ and $h_c$ depend only on the line integrals of the functions g, which in turn depend only on the spatial distribution of the electron density and effective Z along the path of the line integral.

Figure 3:
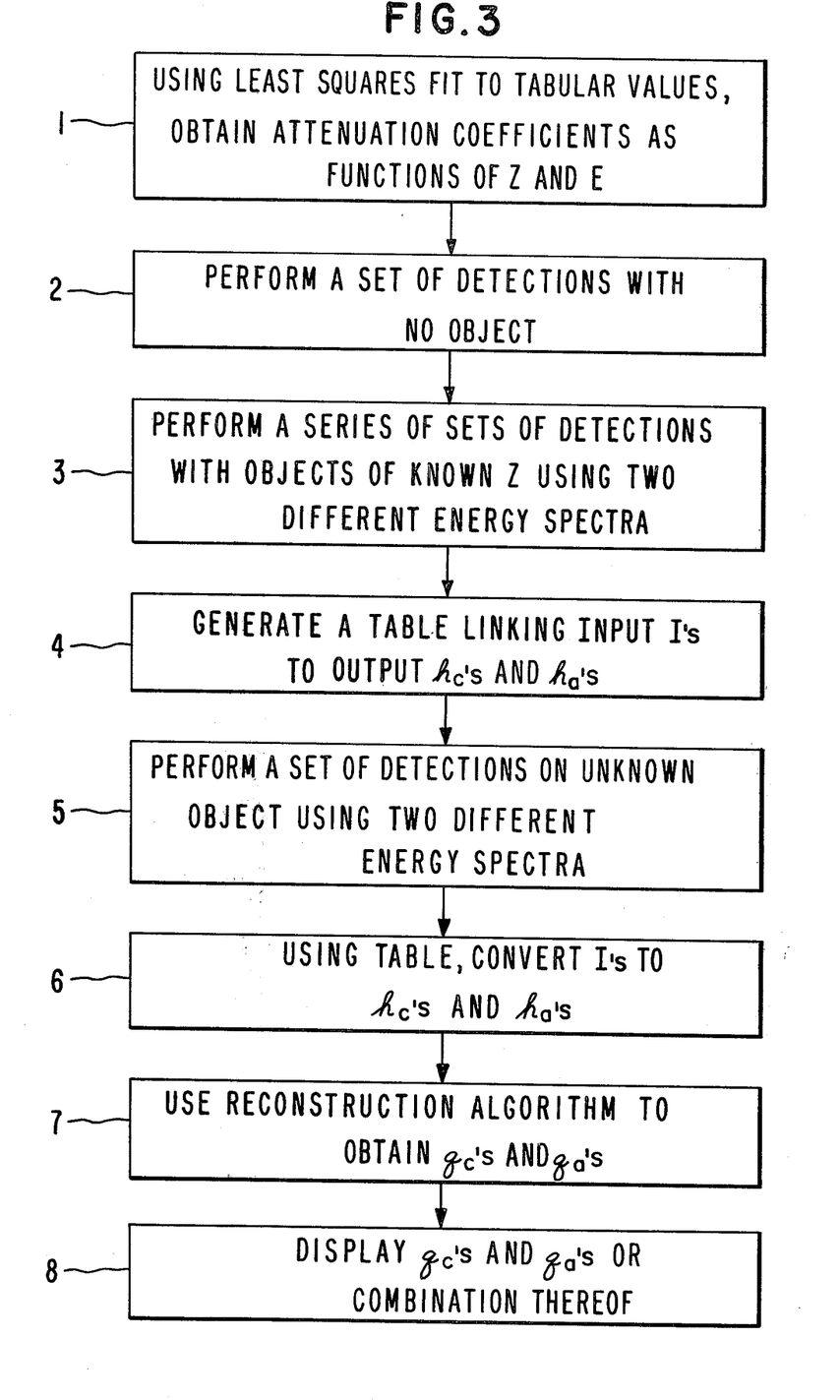
FIG. 3 is a block diagram of the method of the present invention.

We now examine equations 11 and 12. We observe that during the course of a measurement with a fixed function $\Phi(E)$ for the incident flux and with a fixed $\epsilon(E)$ for the detector efficiency we obtain a set of measurements $I_1/I_{01}$ taken in all directions through points drawn in a plane through the object under investigation. We can similarly obtain a set of measurements of the ratio $I_2/I_{02}$ in equation 12. Given this measurement data we can now substitute the measured values of $I_1/I_{01}$ and $I_2/I_{02}$ into equations 11 and 12 for each line through the sample under investigation, and thus obtain a set of two implicit equations with two unknowns $h_a$ and $h_c$. Solution of these equations for $h_a$ and $h_c$ for all directions through all points in the sample under investigation gives a set of data for the line integrals of the functions $q_a$ and $q_c$ given in equations 10. By analogy between equations 10 and 2 this set of data can now be used to reconstruct the spatial dependence of the functions $q_a$ and $q_c$. Substitution in equation 1 gives (Box 7 of FIG. 3)

$$q_c(\vec{R}) = -\frac{1}{\pi} \int dr_1 \frac{1}{r_1} \frac{d}{dr_1} \left( \frac{1}{2\pi} \int_0^\pi d\alpha_1 h_c(\theta,\beta) \right) \quad (13)$$

and $$q_a(\vec{R}) = -\frac{1}{\pi} \int dr_1 \frac{1}{r_1} \frac{d}{dr_1} \left( \frac{1}{2\pi} \int_0^\pi d\alpha_1 h_a(\theta,\beta) \right) \quad (14)$$

Using a reconstruction technique, such as the convolution technique referenced above, we can thus obtain values of $q_a$ and $q_c$ at each point throughout the plane of the sample under investigation. As described above, the q's depend only on the value of the effective Z and the electron density of the material at the point in question. Therefore, using the reconstruction technique on equations 13 and 14 it is possible to obtain the spatial distribution of the effective Z and of the electron density of material throughout the entire plane of the object under investigation.

This formally concludes the description of a technique for the solution of the X-ray emission spectrum problem in transverse axial tomography using a standard medical X-ray tube. In following sections we shall discuss a number of embodiments in regard to the use and accuracy of this technique.

After one has obtained the spatial distribution of the electron density and the effective Z, one is at liberty to combine this information into any form which is desired to best illustrate the information content (Box 8 of FIG. 3). For example, one can combine this information in such a way as to obtain the effective X-ray attenuation density as would be observed by means of a standard X-ray attenuation photograph perpendicular to the plane in question. This would present the information in a form which at the present time is the standard format for viewing X-ray diagnostic information. Now that explicit information on spatial density and effective Z distributions are available this may, in fact, not be the most beneficial way to present the available information. In section II, infra, we present a general discussion of various possible techniques of presentation of this data and also give consideration to the question of the accuracy of the reconstructed images.

In section VII we discuss the use of the waterbag technique and compare the results of that technique with results which can be obtained from the above technique. Of central importance in the application of the above technique is the required solution of equations 11 and 12 for $h_a$ and $h_c$ given in ratios of intensities. This problem is discussed in sections IV - VI. In those sections we describe experimental calibration techniques and their optimization and also present the results of computer studies of the calibration technique and accuracies which can be obtained.

II. FRAMES FOR DATA PRESENTATION

In the preceding section we have described a technique through which data are collected and convolved to obtain the spatial distribution of the functions $q_a(\vec{R})$ and $q_c(\vec{R})$ as given in equations 13 and 14. Once the convolution is completed and one has available these two functions, it is possible to display the results in terms of parameters different from $q_a$ and $q_c$. In this section we discuss a number of such possibilities and also discuss the statistical error associated with the presentation of these data in the various coordinate frames.

First of all, one can present the results in terms of values or gray scale images of the convolution coordinates $q_a$ and $q_c$ as a function of position. These coordinates take on physical significance through equation 7 and represent the energy independent portions of the x-ray coherent (i.e., Compton) scattering and photoelectric absorption densities, respectively. However, the exact physical meaning of this presentation is perhaps not ideal from the point of view of a medical application.

As will be described in later paragraphs, it is possible to combine the functions $q_a$ and $q_c$ in such a manner as to obtain an image which is essentially equivalent to the standard x-ray attenuation density as illustrated by standard x-ray attenuation imaging techniques. First, however, we point out that as a result of the spectrally independent image reconstruction techniques described above, we now have at our disposal more information than has previously been available. A coordinate system for data presentation which may be of considerable value is obtained through the examination of equations 9. By using these equations we can, in fact, solve for the spatial distribution of the effective charge $\overline{Z}(\vec{R})$ and of the electron (mass atomic) density $\overline{\rho}(\vec{R})$ throughout the region for which we have values for the functions of $q_a(\vec{R})$ and $q_c(\vec{R})$. The resulting equations which we obtain are $$\overline{Z}(\vec{R}) \cong \{q_a(\vec{R})/q_c(\vec{R})\}^{1/3.5} \quad (15)$$

and $$\overline{\rho}(\vec{R}) \cong \{q_c(\vec{R})\}^{4.5/3.5}/\{q_a(\vec{R})\}^{1/3.5} \quad (16)$$

for the spatial distribution of the effective charge $\overline{Z}$ and the spatial distribution of the electron density $\overline{\rho}$. Using equations 15 and 16, it is, therefore, possible to display images which illustrate the effective charge distribution and also the electron density distribution throughout the section under investigation. Presentation of the data in this form, particularly the image representing the effective charge spatial distribution, may be of considerable interest and value. It should be pointed out that this form of presentation eliminates one of the significant problems in measurements using standard techniques in that it is no longer possible to mask out the effect of increasing the effective charge Z by a compensating decrease of electron density.

To discuss the above in a more general form, we note that we can consider data presentation coordinates of two general functions $F_1(q_a, q_c)$ and $F_2(q_a, q_c)$. Equations 15 and 16 now form only a special case in which we have $F_1$ and $F_2$ given by the right hand side of these two equations. Note that for image presentation purposes it is not necessary to define both $F_1$ and $F_2$. Only one of these functions need be defined if only one image is desired. As will be discussed later, it may be possible to find by judicious choice some functional form of $F_1$ which minimizes the effect of statistical and other errors and maximum display of particular physiological properties of interest.

Other functional forms of $(R) = Fq\alpha$ may be considered include the following:

$$F_1(\vec{R}) = \ln q\alpha(\vec{R}) \quad (17)$$

$$F_1(\vec{R}) = \ln q_a(\vec{R}) - \ln q_c(\vec{R}) \qquad (18)$$

$$F_1(\vec{R}) = Z^{3.5}(\vec{R}) = q_a(\vec{R})/q_c(\vec{R}) \qquad (19)$$

$$F_1(\vec{R}) = q_a(\vec{R}) \cdot q_c(\vec{R}) \qquad (19a)$$

In the next section we present a discussion of the contribution of the statistical errors in the measurement to the statistical error of the data presentation coordinates $F_1$ and $F_2$. However, first we discuss techniques by which the data content of $q_a$ and $q_c$ can be manipulated to obtain data presentation in terms of effective X-ray attenuation coefficients equivalent to those which are presently in use.

Depending upon how one would like to view the results of transverse axial tomography several functional definitions which could be called the standard effective X-ray attenuation density are available. One definition of an effective density which we call the thin sample effective density can be represented by the equation:

$$D_\delta(\vec{R} \mid \Phi) = \frac{\int \Phi(E) \epsilon(E) G_c(E) q_c(\vec{R}) dE + \int \Phi(E) \epsilon(E) G_a(E) q_a(\vec{R}) dE}{\int \Phi(E) \epsilon(E) dE} \qquad (20)$$

As can be seen by reviewing the above equation, this effective density represents the average X-ray absorption density which would be measured using an X-ray beam with an energy spectrum given by $\Phi(E)$ in passing through an infinitely thin distance of material whose properties are represented by $q_a$ and $q_c$. Another represention of the effective density, the thick sample case, can be defined by the equation $$D_T(\vec{R} \mid \Phi) = \frac{\int \Phi(E) \epsilon(E) G_c(E) e^{-(G_a h_a + G_c h_c)} q_c(\vec{R}) dE + \int \Phi(E) \epsilon(E) G_a(E) e^{-(G_a h_a + G_c h_c)} q_a(\vec{R}) dE}{\int \Phi(E) \epsilon(E) e^{-(G_a h_a + G_c h_c)} dE} \qquad (21)$$

In this equation the exponent accounts for the spectrum modification of the beam upon passage through some finite thickness of T of some material. The quantities $\bar{h}_a$ and $\bar{h}_c$ represent line integrals over this fixed distance. Equation 21 therefore represents the average X-ray attenuation density which would be observed using an X-ray beam with an incident spectrum $\Phi(E)$ passing through a finite thickness T of some material represented by the exponentials in the equation. Of course, before a presentation can be made the (arbitrary thickness T of the material and its composition must be defined. It can be chosen equal to some nominal appropriate value (e.g., the average diameter of the human head and a tissue equivalent material like water).

Having defined effective X-ray attenuation coefficients by equation 20 or 21 and recalling that we have in fact two different X-ray spectra $\Phi$ and $\Phi_f$ (see equation 12) we are now in a position to define a new set of presentation coordinates bases upon the effective attenuation densities. For example, we can simply display the effective density sets $D_\delta(\vec{R} \mid \Phi)$ and $D_\delta(\vec{R} \mid \Phi_f)$ or $D_T(\vec{R} \mid \Phi)$ and $D_T(\vec{R} \mid \Phi_f)$. Other possibilities are to define an overall averaged effective density by the equations $$\bar{D}_\delta(\vec{R}) = \{D_\delta(\vec{R} \mid \Phi) + D_\delta(\vec{R} \mid \Phi_f)\}/2 \qquad (22)$$

$$\bar{D}_T(\vec{R}) = \{D_T(\vec{R} \mid \Phi) + D_T(\vec{R} \mid \Phi_f)\}/2 \qquad (23)$$

In this case, a complimentary display frame which may be of interest is given, respectively, by the equations $$\bar{D}_\delta(\vec{R}) = \{D_\delta(\vec{R} \mid \Phi) - D_\delta(\vec{R} \mid \Phi_f)\}/2 \qquad (24)$$

or $$\bar{D}_T(\vec{R}) = \{D_T(\vec{R} \mid \Phi) - D_T(\vec{R} \mid \Phi_f)\}/2 \qquad (25)$$

When one observes that in equations 20 and 21 $q_a(\vec{R})$ and $q_c(\vec{R})$ can be removed from under the integral sign, it follows that equations 22 to 25 can be considered as another set of alternative definitions of $F_1$ and $F_2$. Also if $\Phi(E)$ and $\Phi_f(E)$ are replaced by $\Phi(E)\epsilon(E)'$ and $\Phi_f(E)\epsilon(E)$ respectively in equations 20 and 21 we have still another set of definitions of effective attenuation density which may have utility.

III. ACCURACY OF RECONSTRUCTED IMAGES

In this section we discuss the statistical noise contributed to the various image representations which were suggested in the previous section, as a result of statistical noise in the measurements used for the reconstruction. The end result of this analysis will be a set of equations from which one can determine the statistical error $\epsilon_F$ for any given functional form of F from the statistical errors $\epsilon_T$ of the X-ray transmission measurements involved in the determination of the reconstructed results. This determination can be performed automatically by computer 100, which can then send a message to the operator informing him of the magnitude of said errors. The operator can then use this information to help determine which presentation frames to employ for highlighting particular materials. Furthermore, these determinations can be used to optimize the measurement technique to obtain maximum information from the procedure.

We begin by defining $I/I_o$ in equation 11 and $I_f/I_{of}$ in equation 12 by $T_1$ and $T_2$, respectively. Based on the discussion in Section I we observe that in fact $h_a$ and $h_c$ can be considered as functions of $T_1$ and $T_2$. Therefore, we rewrite the equations 11 and 12 in the following form.

$$T_1 = \int \Phi_1(E)\epsilon(E) e^{-\{G_a h_a(T_1,T_2) + G_c h_c(T_1,T_2)\}} dE \qquad (26)$$

and $$T_2 = \int \Phi_2(E)\epsilon(E) e^{-\{G_a h_a(T_1,T_2) + G_c h_c(T_1,T_2)\}} dE \qquad (27)$$

where we have assumed that $\Phi_1(E)\epsilon$ and $\Phi_2(E)\epsilon$ have been normalized so that their integrals are unity. For the purposes of this analysis we cast the equations for performing the reconstruction convolution given in equations 13 and 14 into the following form, which flows from the aforementioned patent applications to Pavkovich and to Pavkovich and Nunan.

$$q(\vec{R}) = \qquad (28)$$

$$\frac{1}{N} \sum_P^N \left( -\frac{\pi}{4a} h^{o,p}(T_1^{o,p}, T_2^{o,p}) - \frac{1}{\pi a} \sum_{n_{odd}}^k \frac{1}{n^2} h^{n,p}(T_1^{n,p}, T_2^{n,p}) \right)$$

where $h^{n,p}(T_1^{n,p}, T_2^{n,p})$ is the value of h along a line at the projection angle $\theta_p$ and a distance na from the point of interest. The sample point spacing is a. The total number of projections is N and there are K measurements in each projection. Note that in this equation the $T_1^{n,p}$ and $T_2^{n,p}$ represent the measured transmissions for the nth measurement of the Pth projection, and h is determined using equations 26 and 27. In equation 28 we have temporarily dropped the subscripts a or c from the variables g and h. Now we consider the general functional form $F(q_a, q_c)$ where $q_a$ and $q_c$ depend on the measured $T_1$ and $T_2$ through equations 26 and 27. The statistical error $\epsilon_F$ which results in the determination of F from measurements $T_1$ and $T_2$ which have statistical errors $\epsilon_{T1}$ and $\epsilon_{T2}$ respectively is given by the following equation, which is based on the sum-of-the-squares method of error analysis:

$$\epsilon_F^2 = \sum_{n,p} \left( \frac{\partial F}{\partial q_c} \frac{\partial q_c}{\partial T_1^{n,p}} + \frac{\partial F}{\partial q_a} \frac{\partial q_a}{\partial T_1^{n,p}} \right)^2 \epsilon_{T_1 n,p}^2 + \qquad (29)$$

$$\sum_{n,p} \left( \frac{\partial F}{\partial q_c} \frac{\partial q_c}{\partial T_2^{n,p}} + \frac{\partial F}{\partial q_a} \frac{\partial q_a}{\partial T_2^{n,p}} \right)^2 \epsilon_{T_2 n,p}^2$$

The sums extend over all measurements of the transmissions $T_1$ and $T_2$. Equation 29 can be written in the form $$\epsilon_F^2 = \sum_{n,p} \left\{ \left( \frac{\partial F}{\partial q_c} \frac{\partial q_c}{\partial h_c^{n,p}} \frac{\partial h_c T_1}{\partial T_1} \Big|_{n,p} + \right.\right.$$

$$\frac{\partial F}{\partial q_a} \frac{\partial q_a}{\partial h_a^{n,p}} \frac{\partial h_a}{\partial T_1} T_1 \Big|_{n,p} \right)^2 \left( \frac{\epsilon_{T1}}{T_1} \Big|_{n,p} \right)^2 +$$

$$\left( \frac{\partial F}{\partial q_c} \frac{\partial q_c}{\partial h_c^{n,p}} \frac{\partial h_c}{\partial T_2} T_2 \Big|_{n,p} + \right.$$

$$\left.\left. \frac{\partial F}{\partial q_a} \frac{\partial q_a}{\partial h_a^{n,p}} \frac{\partial h_a}{\partial T_2} T_2 \Big|_{n,p} \right)^2 \left( \frac{\epsilon_{T2}}{T_2} \Big|_{n,p} \right)^2 \right\} \qquad (30)$$

where the values of $\partial h/\partial T$, T, and $\epsilon_T$ are for the ray n,P.

If we assume for the moment that $$\frac{\partial h_c}{\partial T_1} T_1, \frac{\partial h_c}{\partial T_2} T_2, \frac{\partial h_a}{\partial T_1} T_1, \frac{\partial h_a}{\partial T_2} T_2, \frac{\epsilon_{T1}}{T_1}, \text{AND } \frac{\epsilon_{T2}}{T_2}$$

are constant for all measurements, this equation becomes $$\epsilon_F^2 = \left\{ \left[ \frac{\partial F}{\partial q_c} T_1 \frac{\partial h_c}{\partial T_1} + \frac{\partial F}{\partial q_a} T_1 \frac{\partial h_a}{\partial T_1} \right]^2 \left[ \frac{\epsilon_{T1}}{T_1} \right]^2 + \right. \qquad (31)$$

$$\left. \left[ \frac{\partial F}{\partial q_c} T_2 \frac{\partial h_c}{\partial T_2} + \frac{\partial F}{\partial q_a} T_2 \frac{\partial h_a}{\partial T_2} \right]^2 \left[ \frac{\epsilon_{T2}}{T_2} \right]^2 \right\} \sum_{n,p} \left[ \frac{\partial q}{\partial h^{n,p}} \right]$$

where we have used the observation that from equation 28

$$\frac{\partial q_a}{\partial h_a^{n,p}} = \frac{\partial q_c}{\partial h_c^{n,p}} = \frac{\partial q}{\partial h^{n,p}} \qquad (32)$$

The sum in equation 31 can now be obtained from equation 28 in the following manner.

$$\sum_{n,p} \left[ \frac{\partial q}{\partial h^{n,p}} \right]^2 = \frac{1}{N} \left( \frac{\pi}{4a} \right)^2 + \frac{1}{N} \left( \frac{1}{\pi a} \right)^2 \sum_{n_{odd}} \frac{1}{n^4} \qquad (33)$$

Noting that $$\sum_{n_{odd}} \frac{1}{n^4} = \frac{\pi^4}{48} \qquad (34)$$

we obtain $$\sum_{n,p} \left[ \frac{\partial q}{\partial h^{n,p}} \right]^2 = \frac{\pi^2}{12Na^2} \qquad (35)$$

Placing equation 35 into eqn. 31 gives the final result:

$$\epsilon_F^2 = \left\{ \left[ \frac{\partial F}{\partial q_c} T_1 \frac{\partial h_c}{\partial T_1} + \frac{\partial F}{\partial q_a} T_1 \frac{\partial h_a}{\partial T_1} \right]^2 \left[ \frac{\epsilon_{T1}}{T_1} \right]^2 + \right. \qquad (36)$$

$$\left. \left[ \frac{\partial F}{\partial q_c} T_2 \frac{\partial h_c}{\partial T_2} + \frac{\partial F}{\partial q_a} T_2 \frac{\partial h_a}{\partial T_2} \right]^2 \left[ \frac{\epsilon_{T2}}{T_2} \right]^2 \right\} \frac{\pi^2}{12Na^2}$$

This is the desired equation giving the statistical error in F for the relative statistical errors $\epsilon_{T1}/T^1$ and $\epsilon_{T2}/T^2$ in the measurements. It represents the error due to photon statistic artifacts and other RMS artifacts, such as resistor noise. In deriving equation 36 we assumed that the sets of measurements with spectrum $\Phi_1$ (and also $\Phi_2$) are made to the same relative accuracy. Also, certain assumptions were made relative to the $\partial h/\partial T$ T. We now examine these assumptions.

If we take the partial derivative of equation 26 and 27 with respect to $T_1$ and $T_2$ we can solve the resulting equations to obtain:

$$T_1 \frac{\partial h_c}{\partial T_1} = \frac{\int \Phi_1 \epsilon + dE \cdot \int \Phi_2 \epsilon G_a + dE}{\int \Phi_1 \epsilon G_a + dE \cdot \int \Phi_2 \epsilon G_c + dE - \int \Phi_1 \epsilon G_c + dE \cdot \int \Phi_2 \epsilon G_a + dE} \qquad (37)$$

where $t = e^{-(G_c h_c + G_a h_a)}$ \qquad (38)

The other partial derivatives can be obtained by applying either or both of the following operations to equation 38: (i) interchanging the subscripts 1 and 2, (ii) interchanging the subscripts a and c.

In our derivation of eqn. 36 we essentially assumed that the right hand side of equation 37 is constant independent of $h_a$ and $h_c$. This is not generally true. However, it is true for some special cases. For example, if $\Phi_1$ and $\Phi_2$ are Dirac delta functions at energy $E_1$ and $E_2$ then t cancels from the numerator and denominator of equation 37. In section V we describe numerical calculations with some typical spectra for $\Phi_1$ and $\Phi_2$ over a variety of materials and values for $h_a$ and $h_c$ as given in equation 10. In these calculations we observe only slow variation of the various T $\partial h/\partial T$ functions.

IV. Least-Square Fit of Rayleigh, Compton & Photoelectric X-ray Cross-Sections.

In section VI we describe experimental calibration techniques for use in the application of the spectrally independent transverse axial tomography analysis method. To apply this calibration technique an accurate analytical representation of the measured X-ray cross-sections is required. In this section we present a summary of a least-square fitting program which has been used to fit the measured Rayleigh, Compton and Photoelectric cross-sections for elements having charge from $Z=4$ to $Z=20$ in the X-ray range from 20 to 150 KeV. In this X-ray energy region these three processes give a rather complete description of the process of attenuation of X-ray beams in the passage through matter. Only small coherent scattering effects which depend upon the molecular and crystalline structure have been neglected in detail. However, the integral effects should be properly accounted for in the cross-section formulas presented below. The results which we present here are adequate for use in the experimental calibration procedure described in section VI. They will in addition be used in the following sections for the purposes of a computer analysis and estimate of the statistical accuracy of image reconstructions achievable using the spectrally independent transverse axial tomography analysis technique. Program 1 is a FORTRAN program which was written and used to obtain an accurate least square parameterization of X-ray cross/sections/-tabulated in NBS Bulletin 29 ("Photon Cross Sections, Attenuation Coefficients, and Energy Absorption Coefficients from 10 keV to 100 GeV," U.S. Department of Commerce, National Bureau of Standards, August, 1969.)

In this NBS Bulletin the individual components for the Rayleigh and Compton scattering and photoelectric absorption X-ray cross-sections for elements are given as a function of incident X-ray energy. In the program the total cross-section comprising the sum of the three components has been fitted using the following analytical expressions:

$$\sigma(E,Z) = G_c(E) f_c(Z) + G_a(E) f_a(Z) \tag{39}$$

where $G_a(E)$, $G_c(E)$, $f_a(Z)$ and $f_c(Z)$ are given by the following expressions:

$$G_a(E) = FAE(E) + FR2E(E) \tag{40}$$

where $$FAE(E) = E^{-3} \sum_{n=1}^{7} \mu'_a(n)((E-E_o)/E_o)^{n-1} \tag{41}$$

$$FR2E(E) = (E_o/E)^2 \sum_{n=1}^{4} \mu'_R(n)(E - E_o)^{n-1} \tag{42}$$

$$G_c(E) = GSUBC(E) + FR1E(E) \tag{42a}$$

where $$GSUBC(E) = \tag{43}$$

$$\frac{8\pi \times 7.9398 \times 10^{-2}}{3(1 + 2E/511)^2} \Big(1 + 2E/511 + \frac{6}{5}(E/511)^2 -$$

$$\frac{1}{2}(E/511)^3 + \frac{2}{7}(E/511)^4 - \frac{6}{35}(E/511)^5\Big)$$

$$FR1E(E) = (E_o/E)^2 \sum_{n=1}^{3} \mu_R(n)(E - E_o)^{n-1} \tag{44}$$

$$f_a(Z) = FAZ(Z) \tag{45}$$

where $$FAZ(Z) = Z^{4.5} \sum_{n=1}^{7} \mu_a(n)((Z - Z_o)/Z_o)^{n-1} \tag{46}$$

and $$f_c(Z) = Z \tag{47}$$

For convenience we have also included the FORTRAN variables (equations 41, 42, 43, 44, and 46) for these functions which have been used in the FORTRAN program. The arrays $\mu_a(n), \mu'_a(n), \mu_R(n)$ and $\mu'_R(n)$ are parameters determined by the least-square program. The parameters $Z_o$ and $E_o$ are fixed input parameters. For example, the total cross-section SIGTH is calculated using these expressions in the program.

We here briefly describe the procedure used in the program for the parameterization of the total X-ray attenuation cross-section. The various components in the equations 39 to 47 have their origin from the following expressions for the basic X-ray cross sections.

$$\sigma_a(E,Z) = FAZ(Z) * FAE(E) \tag{48}$$

$$\sigma_c(E,Z) = Z * GSUBC(E) \tag{49}$$

$$\sigma_R(E,Z) = FAZ(Z) * FR2E(E) + FR1E(E) \tag{50}$$

where $\sigma_a$ is the photoelectric cross-section, $\sigma_c$ is the Compton cross-section and $\sigma_R$ is the Rayleigh scattering cross-section. In the program the first step in the procedure is to determine a set of parameters which best fit the absorption cross-section using the functional form given in equation 48. The expression for the Compton scattering cross-section given in equation 49 is in fact an exact analytical expression which fits this portion of the X-ray cross-section without further fitting. The next step in the program is, therefore, to fit the Rayleigh scattering cross-section using the expression given in equation 50 where we hold the parameters $\mu_a(n)$, which were determined in the fit of the absorption cross-section $\sigma_a$, constant. Upon completion of this procedure we have a complete set of parameters from which the total X-ray attenuation cross-section given in equation 39 can be calculated. In obtaining the results which will be presented below the above procedure was iterated a number of times in order to determine the best possible set of parameters.

Using the above program and the procedure which has been described the following parameters were obtained which can be used in equations 39 to 47 for calculation of the total X-ray attenuation cross-section.

|  | $Z_o = 6.5$ | $E_o = 75$ Kev |
| --- | --- | --- |
| $u_A(1) = 1.000$ | $u_A'(1) = 7.832$ | $u_R(1) = 0.1513 \times 10$ |
| $u_A(2) = 0.3245$ | $u_A'(2) = -1.621$ | $u_R(2) = 0.1100 \times 10$ |
| $u_A(3) = 0.5507 \times 10$ | $u_A'(3) = 4.289$ | $u_R(3) = -.9817 \times 10$ |
| $u_A(4) = -1.512$ | $u_A'(4) = 8.140$ | $u_R'(1) = 0.3296 \times 10$ |
| $u_A(5) = 2.378$ | $u_A'(5) = -3.226$ | $u_R'(2) = -0.2151 \times 10$ |
| $u_A(6) = -1.444$ | $u_A'(6) = -9.871$ | $u_R'(3) = 0.4415 \times 10$ |

| $u_A(7) = 0.3014$ | $u_A'(7) = 2.189$ | $u_R'(4) = 0.2832 \times 10$ |
|---|---|---|

The discussion under this heading corresponds to Block 1 on the FIG. 3 flow chart.

V. COMPUTER STUDY OF STATISTICAL ACCURACY IN SITAT.

In this section we discuss a FORTRAN program, Program 2, which has been prepared to analyze the statistical accuracy of results presented in various presentation frames discussed in section II. The basic formulations required for this analysis were presented in section III. Specific calculations have been made for the statistical error in presentation frames represented by equations 15 and 16, and also 21. In addition, parameters corresponding to certain terms in equation 36 have been evaluated (e.g., equations 53 or 57) so that the statistical accuracy in a presentation frame represented by the equation $F(q_a, q_c)$ as discussed in section II can easily be calculated. In the following paragraphs we discuss the flow of the program and the results which are obtained.

In addition to calculating the results related to statistical error in the SITAT technique, the program also conveniently calculates certain computer generated data suitable for test of the calibration procedure relating to the solutions of equations 11 and 12 for $h_a$ and $h_c$ and the related experimental calibration techniques for obtaining these solutions from data obtained in an actual instrument. A description of the formulation used in the program to calculate these computer generated data will be presented in this section; however, the detailed discussion of their significance and use for testing the calibration procedure is presented in section VI along with the description of the procedure itself.

As was discussed in section III, in order to determine the statistical error in a presentation represented by the function F, we use equation 36. Of central significance in using this equation to calculate the error are the partial derivatives of the form $T\partial h/\partial T$ which are obtained using equation 37. An examination of this equation shows that these partial derivatives are calculated from integrals over the spectra $\Phi_1$ and $\Phi_2$ of the following form.

$$TSPEC = T = \int \Phi_i \kappa_i t \, dE \tag{51}$$

(see also equation 26 and 27) and $$TIG\alpha I = \int \Phi_i \kappa_i t G\alpha \, dE \tag{52}$$

where $t$ is given by equation 38.

The left hand members of these equations give the names of the FORTRAN variables used in the program for these parameters. The subscript i in the other equations numbers the spectrum over which the integral is being performed and the subscript $\alpha$ is either a or c. With these definitions the variables in the right hand portion of the above equations have been previously defined in developing equations 37 and 38. The significance of the notation on the left hand side will be better defined later. In Program 2, the FORTRAN program which we will describe in more detail later, the integrals represented by equations 51 and 52 are calculated. These results and equation 37 are used to obtain results of the form $$PD\alpha T = T\frac{\partial h\alpha}{\partial \tau}\sqrt{\frac{\pi^2}{12\,N a^2}} \tag{53}$$

where the left hand side are the names of FORTRAN variables calculated by the program. A comparison of the right hand side of equation 53 and equation 36 will show that given the numerical values of the variables represented by equation 53 the only pieces of information required to calculate the statistical error in the function $F(q_a, q_c)$ are the partial derivatives F with respect to qa and qc and the relative error in the measured transmissions.

We now give a summary of the procedure used by the program to evaluate the parameters represented by equations 51, 52 and 53. We also include details on the numerical values for the parameters which were used in the calculations of the results.

The calculations in Program 2 are based on the assumption of uniform density samples of material. The results are calculated for various atomic numbers and various lengths L. We also assume a detector efficiency equal to unity. The cross-sections used in the program are based upon the least-square fit which was discussed in section IV. In the program numerical integrations were performed over three incident X-ray spectra. These spectra correspond to experimentally observed spectral distributions from X-ray tubes operated at 70, 100, and 130 kV DC potential. The results are then presented in terms of the spectrum pairs: (70, 100), (70, 130), and (100, 130). The option for calculating a filtered spectrum as a result of passage through an X-ray filter of some type is also incorporated in the program. However, for the results to be presented here a unity transmission filter has been assumed. Based on these assumptions and using equations 10 and 39 and realizing that q (see equation 7) is equal to the density times the function f in equation 39, one can perform the integrals and calculations required to calculate the right hand terms of equations 51 and 52.

The numerical values for the spectral distributions $\phi_i$ will not be listed here. The numerical value used in the program for N is 360 and for a is 0.3 cm. The terms for the error in transmission $\epsilon_{T1}/T_1$ and $\epsilon_{T2}/T_2$ were assumed to be given by expressions of the following general form.

$$\frac{\epsilon_T}{T} = \frac{1}{\sqrt{I_o T}} \tag{54}$$

This expression is obtained by observing that $$T = I/I_o \tag{55}$$

and, therefore, $$\frac{\epsilon_T}{T} = \frac{\epsilon_I}{TI_o} = \frac{\sqrt{I}}{TI_o} = \frac{\sqrt{T}\,I_o}{TI_o} = \frac{1}{\sqrt{I_o T}} \tag{56}$$

We have assumed that the error in $I_o$ is negligible. For the calculation we assume an incident flux I of $10^8$ photons per measurement. Note that this assumption does not necessarily optimize the total length of time required for a measurement. In order for the optimization to obtain a minimum statistical error $\epsilon_F$ in F in a given total length of time for the measurement, the relative magnitude of the two terms in equation 36 must be compared.

Using these assumptions one can simplify the calculation of equation 36 for the error in F even further than that achieved by using equation 53 by means of using the values of the parameters:

$$ERaN = PDaT\frac{\epsilon_T}{T} = T\frac{\partial h_\alpha}{\partial T}\sqrt{\frac{\pi^2}{12Na^2}}\frac{1}{\sqrt{I_oT}} \qquad (57)$$

calculated by the FORTRAN program. With this result only the partial derivatives of F with respect to $q_a$ and $q_c$ are required to evaluate equation 36.

Using the results of the above calculation, the program then calculates statistical error evaluations for the specific presentation formulas given by equations 15 and 16. These are labeled by the parameters ERZSZ and ERRSR, respectively, in the program. Using equation 57, 15 in 36, we obtain the following expression for the relative error in atomic number:

$$\frac{\epsilon_{Z(R)}}{Z} = ERZSZ = \qquad 58$$

$$\frac{1}{3.5}[\{ERAN_1 - ERCN_1\}^2 + \{ERAN_2 - ERCN_2\}^2]^{\frac{1}{2}}$$

where the subscripts refer to spectra $\Phi_1$ and $\Phi_2$. And using equation 57, 16 in 36, we obtain the following expression for the relative error in electron density:

$$\frac{\epsilon_{\rho(R)}}{\rho} = ERRSR = \qquad (59)$$

$$\frac{1}{3.5}[\{ERAN_1 - 4.5\,ERCN_1\}^2 + \{ERAN_2 - 4.5\,ERCN_2\}^2]^{\frac{1}{2}}$$

$$\quad qa \qquad qc \qquad\qquad qa \qquad qc$$

In addition, the program calculates the error EREFON in the effective density as given in the presentation frame represented by equation 23. This is an interesting presentation frame in that the formulation of the error given by equation 36 can be considerably simplified as follows.

First we consider the representation for effective density given by equation 21, where we consider $\Phi$ to be $\phi_1$. That is, F in equation 36 is taken to be equal to $D_T(\bar{R},\Phi_1)$ as given by equation 21. If we now take the partial derivatives of F with respect to $q_a$ and $q_c$ as required in equation 36, and also substitute results of equation 37, we obtain $$\epsilon_F^2 = \epsilon_{DT}^2 = \frac{\pi^2}{12Na^2}\left(\frac{\epsilon_{T1}}{T_1}\right)^2 \qquad (60)$$

where $\epsilon_{DT}$ is equal to the statistical error in D given by equation 21 due to the relative statistical errors in the measured transmission. In the derivation of equation 60 we have assumed that $h_a$ and $h_c$ in equation 38 are approximately equal to $\bar{h}_a$ and $\bar{h}_c$ of equation 21. This results in the apparent independence of the error in $D_T(\bar{R},\Phi_1)$ on the error $\epsilon_{T2}$. To obtain the dependence on $\epsilon_{T2}$ one must consider second order terms: If one supposes that $$h_c = \bar{h}_c(1+\Delta_c) \qquad (61)$$

and $$h_a = \bar{h}_a(1+\Delta_a) \qquad (62)$$

then one obtains $$\epsilon_{DT}^{\prime 2} = \frac{\pi^2}{12Na^2}\left(\frac{\epsilon_{T2}}{T_2}\right)^2 \{\Delta_c h_c[\int\Phi_1\epsilon G_a \mp dE \cdot \int\Phi_2\epsilon G_c^2 \mp dE - \qquad (63)$$

$$\int\Phi_1\epsilon G_c \mp dE \cdot \int\Phi_2 E G_a G_c dE]$$

$$+ \Delta_a h_a[\int\Phi_1\epsilon\bar{G}_a \mp dE\int\Phi_2\epsilon G_a G_c \mp dE -$$

$$\int\Phi_1\epsilon G_c \mp dE\int\Phi_2\epsilon G_a^2 dE]\}/$$

$$\{\int\Phi_2\epsilon G_a \mp dE\int\Phi_1\epsilon G_c \mp dE - \int\Phi_2\epsilon G_c \mp dE\int\Phi_1\epsilon G_a \mp dE\}$$

where $\epsilon_{DT}^{\prime 2}$ is the contribution of statistical error in $T_2$ to the statistical error of $D_T(\bar{R},\phi_1)$.

Some rough estimates of this quantity indicate this contribution is less than 10% of the magnitude of the contribution expressed in equation 60 for the expected values of the various parameters.

Using results of the form expressed in equation 60 we now can obtain directly the expression for the error in the overall average effective density as described in equation 23.

$$\epsilon_{\bar{D}T} = \frac{1}{2}\sqrt{\frac{\pi^2}{12Na^2}\left\{\left(\frac{\epsilon_{T1}}{T_1}\right)^2 + \left(\frac{\epsilon_{T2}}{T_2}\right)^2\right\}} \qquad (64)$$

IF $$\epsilon_{T1}/T_1 \cong \epsilon_{T2}/T_2$$

THEN $$EREFDN = \frac{1}{\sqrt{2}}\sqrt{\frac{\pi^2}{12Na^2}}\frac{\epsilon_{T1}}{T_1} \qquad (65)$$

EREFDN is the name of the FORTRAN variable.

The above discussion completes the description of the application of the FORTRAN program for analysis of the statistical error in the SITAT technique. In the following we summarize and define certain parameters which are calculated by the program which serve as computer generated data for application and test of the calibration procedures described in section VI. For each charge, thickness, and spectrum pair, 4 parameters are calculated by the program. These four parameters are $$BLOGT = \ln\int\Phi_i\epsilon tdE \qquad (66)$$

$$RLTSLT = \ln\int\Phi_1\epsilon tdE/\ln\int\Phi_2\epsilon tdE \qquad (67)$$

$$HSUBC/LOGT2*LOGT1 = h_c/\{\ln(\int\Phi_1\epsilon tdE)\cdot\ln(\Phi_2\epsilon tdE)\}^{\frac{1}{2}} \qquad (68)$$

$$HSUBA/LOGT2*LOGT1 = h_a/\{\ln(\int\Phi_1\epsilon tdE)\cdot\ln(\int\Phi_2\epsilon tdE)\}^{\frac{1}{2}} \qquad (69)$$

VI. EMPIRICAL CALIBRATION TECHNIQUES FOR SITAT

In section I we described the spectrally independent transverse axial tomography technique for image reconstruction. It requires the solution of equations 11 and 12 for $h_a$ and $h_c$ given the experimentally measured intensity ratios $I_1/I_{01}$ and $I_2/I_{02}$. In this section we present an empirical technique through which the calibration of a specific machine having characteristic spectra $\Phi_1$ and $\Phi_2$ and detector efficiency $\epsilon(E)$ is accomplished and the inversion of the two equations for $h_a$ and $h_c$ is performed. As will become evident, detailed knowledge of the spectral functions representing the incident X-ray spectra $\Phi_1$ and $\Phi_2$ and the detector efficiency with respect to energy is not necessary. It is sufficient to know integral information which can be obtained by experimental measurements on the specific device for the calibration.

We begin by observing that through equation 10 the values of $h_a$ and $h_c$ can be calculated for samples of materials of known atomic composition (for example, particular elements or compounds), known density, and given length. In equation 10, $q_a$ and $q_c$ are given by the product of the electron density and $f_a$ and $f_c$ respectively, as defined in equation 39. Therefore, through the selection of a series of materials of known uniform chemical composition (for example, beryllium, carbon, water, aluminum, and titanium) and using samples of a variety of lengths, it is possible to obtain samples with varying values of $h_a$ and $h_c$ over the entire range of interest for these parameters. Using the specific device to be calibrated these samples can be placed in the beam corresponding to the spectrum $\Phi_1$ and the spectrum $\Phi_2$ and the intensity ratios $I_1/I_{01}$ and $I_2/I_{02}$ of equations 11 and 12 can be measured (Boxes 2 and 3 of FIG. 3). This set of data corresponds to a complete set of empirical data which can be used for calibration of the specific device. In principle this data could be tabulated in tables giving $h_a$ or $h_c$ as a function of the values of the measured intensity ratios $I_1/I_{01}$ and $I_2/I_{02}$ (which we denote as the transmissions $T_1$ and $T_2$ henceforth (Box 4 of FIG. 3). See equations 26 and 27). Having prepared such a table it would then be possible to determine the value of $h_a$ and $h_c$ for an unknown sample by a measurement of $T_1$ and $T_2$ (Boxes 5 and 6 of FIG. 3). This then completes the calibration procedure and provides us with the required results.

Various modifications of this calibration procedure are possible. For example, consider the case in which the calibration procedure described above is performed with a standard normalizing phantom (consisting of a uniform circular disk of water for example) placed in the apparatus during the measurement of intensities $I$ and $I_0$ with the calibrated samples. The normalizing phantom must lie totally within the radiation beam and be aligned with the axis of rotation of the source-detector assembly. This example is of significant interest because, as will be shown below, the results of the SITAT is then the difference between the uniform material properties of the standard normalizing phantom (water in the example) and the material properties of the anatomical cross section under study. In some cases this technique will reduce the systematic error of the system and produce generally improved results.

The above modification to the calibration technique can be introduced into the mathematics as follows: First one replaces $\Phi_i$ by $\Phi_i T_{H_2O}$ where $T_{H_2O}$ is the transmission of the normalization phantom. Then in equation 11:

$$G_c h_c + G_a h_a = G_c^{H_2O} h_c^{H_2O} - G_c^{Ph} h_c^{(Ph} + G_a^{H_2O} h_a^{H_2O} - G_a^{Ph} h_a^{Ph} \quad (69a)$$

Or, on identifying the various parts:

$$G_c h_c = G_c(h_c^{H_2O} - h_c^{Ph}) \quad (69b)$$

$$G_a h_a = G_a(h_a^{H_2O} h_a^{Ph}) \quad (69a)$$

In the calibration measurement using the $H_2O$ standard normalizing phantom and the calibrated samples we have:

$$G_c^{Ph} h_c^{Ph} = G_c^{H_2O} h_c + G_c^{SAMPLE} h_c^{SAMPLE} \quad (69d)$$

$$G_a^{Ph} h_a^{Ph} = G_a^{H_2O} h_a + G_a^{SAMPLE} h_a^{SAMPLE} \quad (69e)$$

Placing these equations into equations 69B and 69C;

$$G_c h_c = G_c^{SAMPLE} h_c^{SAMPLE} \text{ OR } h_c = h_c^{SAMPLE} \quad (69f)$$

$$G_a h_a = G_a^{SAMPLE} h_a^{SAMPLE} \text{ OR } h_a = h_a^{SAMPLE} \quad (69g)$$

Thus, one finds that only $h_c$ and $h_a$ for the sample are required to be known and that the properties of the normalizing phantom need not be known for the purpose of calibration. Using this technique one can proceed as described in paragraph three of this section and the results of the reconstruction from equation 13 are:

$$q_a^{Ph} - q_a \text{ normalizing phantom}$$

and $$q_c^{Ph} - q_c \text{ normalizing phantom}$$

From the above, we see that the results of the measurement are the differences between the properties of the normalizing phantom and the anotomical cross section under consideration.

In the following paragraphs we outline a procedure for obtaining an empirical fit to the measured calibration data which in turn can be used to directly calculate the parameters $h_a$ and $h_c$ for an unknown sample with measured transmission $T_1$ and $T_2$. A closer examination of equations 11 and 12 indicates that very rapid exponential type variations exist in the relationships between the h parameters and transmission parameters. For ease of establishing an empirical fit, the following parameter transformation is useful. We define the four parameters $S_a$, $S_c$, $x$, $y$ as follows:

$$S_a = h_a / \{\ln \int \Phi_1 \epsilon t dE \ln \int \Phi_2 \epsilon t dE\}^{\frac{1}{2}} = h_a/(\ln T_1 \cdot \ln T_2)^{\frac{1}{2}} \quad (70)$$

$$S_c = h_c / \{\ln \int \Phi_1 \epsilon t dE \ln \int \Phi_2 \epsilon t dE\}^{\frac{1}{2}} = h_c/(\ln T_1 \cdot \ln T_2)^{\frac{1}{2}} \quad (71)$$

$$x = \ln \int \Phi_1 \epsilon t dE = \ln T_1 \quad (72)$$

$$y \ln \int \Phi_1 \epsilon t dE / \ln \int \Phi_2 \epsilon t dE = \ln T_1 / \ln T_2 \quad (73)$$

Given the above calibration data a table can be prepared which represents the inter-relationship between these four parameters and the required solutions for equations 11 and 12 can be represented as the functions $$S_a = S_a(x,y) \quad (74)$$

and $$S_c = S_c(x,y) \quad (75)$$

Given these relationships and measured values $T_1$ and $T_2$ one can use equations 72 and 73 to calculate x and y, then one can evaluate $S_a$ and $S_c$ through the use of equations 74 and 75 and in turn obtain $h_a$ and $h_c$ from equations 70 and 71. For practical spectra $\Phi_1$ and $\Phi_2$ and detector efficiency $\epsilon$, the functions represented by equations 74 and 75 are relatively slowly varying and can be well approximated by polynomial expansion.

At least square fitting program was prepared which evaluates the coefficients of a polynomial expansion representing equations 74 and 75 as follows.

$$S_a(x,y) = \sum_{j=1} \sum_{i=1} A_{aij} x^{i-1} y^{j-1} \tag{76}$$

$$S_c(x,y) = \sum_{j=1} \sum_{i=1} A_{cij} x^{i-1} y^{j-1} \tag{77}$$

Given a set of calibration data this probram can be used to calculate the coefficients $A_{aij}$ and $A_{cij}$ in these equations. This completes the description of the empirical calibration procedure which has been developed for use in the SITAT technique.

As a test of the technique, the program has been applied to computer generated calibration data based on NBS tables as follows. As was indicated in the preceding section, Program 2 calculated certain parameters outlined in equations 66 through 69. An examination of these equations will in fact show that these parameters are the equivalent to the parameters x, y, $S_a$ and $S_c$ as described in equations 70 through 73 above and are, therefore, directly applicable as input data for Program 3, the program described in this section.

$$I_{01} = \int \Phi'(E) dE \tag{80}$$

In these equations the effective flux $\Phi'(E)$ is given by the equation $$\Phi'(E) = \Phi_1(E)\epsilon(E)e^{-L\sigma_H(E)\rho_H} \tag{81}$$

and $$\Delta(E) = \int_0^L \{ \rho(l) \sigma [E, Z(l)] - \rho_H \sigma_H(E) \} dl \tag{82}$$

In the above equations $\sigma_H$ and $\rho_H$ represent the X-ray cross section and electron density of water, and $\sigma$ and $\rho$ represent the X-ray attenuation cross section and the electron density of the unknown object under investigation.

If we assume $\Delta$ is small, the ratio of equation 79 to equation 80 can be expanded to obtain $$\frac{I_1}{I_{01}} \approx 1 - \frac{\int \Phi^1 \Delta dE}{\int \Phi dE} + \frac{\int \Phi^1 \Delta^2 dE}{2! \int \Phi^1 dE} - \tag{83}$$

Upon defining the effective attenuation density by $$\bar{\Sigma}(l) = \frac{\int \Phi^1(E)\{\sigma[E,Z(l)]\rho(l) - \rho_H \sigma_H(E)\} dE}{\int \Phi^1(E) dE} \tag{84}$$

and the mean square effective attenuation density by $$\bar{\bar{\Sigma}}^2(l) = \frac{\int \int \Phi^1(E)\{ \sigma[E,Z(l)]\rho(l) - \sigma_H(E)\rho_H \} \{ \sigma[E,Z(l^1)]\rho(l^1) - \sigma_H(E)\rho_H\} dE dl^1}{\int \Phi^1(E) dE} \tag{85}$$

VII. DISCUSSION OF THE WATERBAG TECHNIQUE IN TRANSVERS AXIAL TOMOGRAPHY

In this section we give a brief presentation of the use of a water bag technique to reduce the effects of the spectrum problem in transverse axial tomography when using a reconstruction technique which neglects the spectral distribution of the incident X-ray beam. We first formulate this technique and develop formulas which describe the parameters that are measured using this technique. We then discuss briefly the approximate limitations of the technique in terms of the error which results in the reconstructed image due to the approximations made in using the technique. We begin with equations 3 and 4 and note that H can be written as $$H = \int \rho(l)\sigma[E,Z(l)] dl \tag{78}$$

Now, if an experimental apparatus is arranged in such a manner as to perform intensity measurements in such a manner that the $I_{02}$ measurement corresponds to a measurement in which the X-ray beam passes through an effective length L of water and in which the measurement of $I_1$ is a measurement of the object under investigation when placed within a water bath whose external dimension has an effective dimension L, then equations 3 and 4 become $$I_1 = \int \Phi'(E) e^{-\Delta(E)} dE \tag{79}$$

and equation 83 can be written in the form $$I_1/I_{01} = 1 - \int \bar{\Sigma}(l) dl + \frac{1}{2!} \int \bar{\bar{\Sigma}}^2(l) dl - \tag{86}$$

or, neglecting second order terms, $$I_1/I_{01} = e^{-\int \bar{\Sigma}(l) dl} \tag{87}$$

The effective attenuation density represents the attenuation density of the object under study, not including the water bag, averaged over the energy spectrum. In the above equation we note that if the second order and higher terms are neglected, it is possible to obtain measurements for the effective attenuation coefficient line integrals from measurements of $I_1$ and $I_{01}$. Therefore, if measurements of this line integral ae performed at all directions $\theta$ through each pont $\vec{R}$ of an unknown object, an image reconstruction using any reconstruction algorithm can be performed to obtain the effective photon attenuation at each point in the sample. Thus, by comparison with equation 84 we obtain $$\bar{\Sigma}(\vec{R}) = \frac{\int \Phi^1(E)\{ \rho(\vec{R})\sigma[E,Z(\vec{R})] - \rho_H \sigma_H(E)\} dE}{\int \Phi^1(E) dE} \tag{88}$$

Through the use of results that are represented by equation 88 and some straightforward calibration measurements it is possible to obtain the effective photon attenuation at all points throughout the sample under investigation. This effective photon attenuation is represented by the equation $$<\rho\sigma>_{\vec{R}} = \frac{\int \Phi^1(E)\rho(\vec{R})\sigma[E,Z(\vec{R})]dE}{\int \Phi^1(E)dE} \tag{89}$$

This equation then represents the result which can be obtained using the water bag technique in transverse axial tomography.

We now give consideration to an estimate of limitations imposed by the approximations made in arriving at equation 89. A measure of the error in this technique can be obtained by determining the differences between equations 86 and 87 to second order. This second order difference is given by $$\text{DIF} = \frac{1}{2}\left[\frac{\int \Phi^1(E)\{E,l\}\{E,l^1\}dl^1dldE}{\int \Phi^1(E)dE} - \frac{\int \Phi^1(E)\{E,l\}\Phi^1(E^1)\{E^1,l^1\}dldl^1dEdE^1}{(\int \Phi^1(E)d(E))^2}\right] \tag{90}$$

where $$\{E_1l\} = \{\rho(l)\sigma[E,Z(l)] - \rho_H\sigma_H(E)\} \tag{91}$$

If one defines $\bar{\psi}$ using equation $$\bar{\psi}(E) = \int \{E,l\}dl \tag{92}$$

then equation 90 can be written as $$\text{DIF} = \frac{1}{2}\left\{\frac{\int \Phi^1(E)\bar{\psi}^2(E)dE}{\int \Phi^1(E)dE} - [\int \bar{\Sigma}(l)dl]^2\right\} \tag{93}$$

The very rough calculation of this difference gives a value of approximately $4 \times 10^{-5}$ for this difference when a 1% portion of a 24 cm effective water path length is assumed to be air. A review of brain scans indicate that deviations of the order of 6% to 9% from water are observed in integral path lengths through the skull. Therefore, we have an effective second order difference of the order of approximately $6 \times 4 \times 10^{-5} = 2.4 \times 10^{-4}$. Noting that $T = e^{-a}$ or $dT/T = -da$ we conclude that a rough estimate of the error which results from this second order effect in the water bag technique on the reconstructed image can be estimated by substituting the value of Dif given by equation 93 for $\epsilon_T/T$ in equation 60. From the above discussion we conclude that water technique has an apparent minimum systematic error corresponding approximately to an error of $2.4 \times 10^{-4}$ in $\epsilon_T/T$. Therefore, the collection of data for measurements of $I_1$ and $I_{01}$ to statistical accuracy better than approximately 0.03% to 0.05% will not significantly improve the image quality of the reconstructions obtained using this technique. Fairly conservative assumptions were made in deriving this result. The actual effect could be considerably more restrictive.

VIII. TYPICAL EFFECTIVE ELECTRON DENSITIES AND EFFECTIVE CHARGES FOR ANATOMICAL ORGANS AND TISSUE

As was mentioned in Section I, when the object under investigation is composed of chemical compounds, the total attenuation component is the sum due to the individual attenuation components of the elemental constituents in the material. In this section we formulate the techniques and formulas for appropriately accounting for these effects in the results of the previous sections. Then, based on the known chemical composition of various anatomical materials, we calculate and present results which are intended to indicate the fluctuations in the effective electron density and the effective charge which must be measured in order to obtain medically significant images from spectrally independent transverse axial tomography. From the discussion of equation 7 and using equation 39 we observe that we can write the generalized expression $$q = \Sigma f[Z_i(\vec{R})]\rho_i(\vec{R}) \tag{94}$$

where $\rho_i$ is the electron density of the element with charge $Z_i$ at the location $\vec{R}$. The sum is taken over all of the elements which compose the material under study at the point $\vec{R}$. After subscripts a and c have been added to q and f in equation 94 this equation then represents the quantities which are, in fact, measured by the transverse axial tomography technique, and which are determined by the application of a reconstruction algorithm.

We note that in using equation 94 it is possible to define an effective charge $\overline{Z}_f$ as the solution of the following equation $$f[\overline{Z}_f(\vec{R})] = \frac{\Sigma f[Z_i(\vec{R})]\rho_i(\vec{R})}{\rho(\vec{R})} \tag{95}$$

$$\rho(\vec{R}) = = \Sigma \rho_i(\vec{R}) \tag{96}$$

$\overline{Z}_f$ depends upon the functional dependence of the function f; in general, different functional dependencies for f will give different results for the effective charge $\overline{Z}_f$. An assumption for the functional form of f must be made. In the following we assume that equations 9 give this functional dependence. Then, based upon equation 94 we define an effective electron charge density $\overline{Z}\overline{\rho}(\vec{R})$ and an effective charge $\overline{Z}(\vec{R})$ by the equations $$q_c = \overline{Z}\overline{\rho} = \rho \Sigma Z_i \rho_i / \rho \tag{97}$$

and $$q_a = \overline{Z}^{3.5}\overline{\rho} = \rho \Sigma Z_i^{4.5} \rho_i / \rho \tag{98}$$

Using Eqn. 97 in eqn. 98 we obtain $$Z = [\Sigma Z_i^{4.5}\rho_i / \Sigma Z_i \rho_i]^{1/3.5} \tag{99}$$

We can define the effective electron density $\overline{\rho}$ by the equation $$\overline{\rho} = \overline{Z}\rho / \overline{Z} \tag{100}$$

and an average charge as $$<Z> = \Sigma Z_i \rho_i / \rho \tag{101}$$

we also not that the mass density $\rho_m$ is $$\rho_m = \Sigma A_i \rho_i \tag{102}$$

where $A_i$ is the atomic mass of the ith element and is closely related to $q_c$ since $A \sim 2Z$. The above defined quantities are consistent with those discussed in equations 15 and 16 and give a definition annd interpretation of the quantities which were discussed in Section II. Note also that Section V gives calculated estimates of the statistical accuracy which can be obtained in the measurements of these quantities using transverse axial tomography.

A FORTRAN program, Program 4, was developed which calculates the effective charge and average charge density for 18 representative anatomical materials. A set of tables, Table 4, was generated giving results which have been obtained from the program. The effective charge as defined by equation 99 is given along with the relative electron densities for each of the elements in the first 18 tables of Table 4. In the nineteenth table, the percent differences of these effective charge values from a median effective charge (calculated excluding bone) is given. This table shows SITAT accuracies which will be required to distinguish the various materials. Using this chart in conjunction with the known statistical error as determined in the previous sections allows one ro select an appropriate presentation frame for distinguishing between desired anatomical organs. If the difference in effective charge between two organs desired to be distinguished exceeds the known statistical error associated with that presentation frame, then the system is capable of making the desired distinguishment. Computer 100 can be programmed to display which of a preselected list of organs can be distinguished using which presentation frames, and vice versa.

IX. OPTIMIZATON OF MEASUREMENT PARAMETERS

Once the formulation for the error analyses presented in Section III are known, the results can be applied for a variety of purposes. For example, they can be used to study the statistical accuracy of SITAT as presented in Section V. In this section we illustrate another application, one where the results of Section III are applied for optimization of measurement parameters. The set of measurement parameters to be optimized can be aribitrarily chosen. In the example for this section we have chosen the following parameters: We assume that the two required spectra are generated by measurements with and without a filter in a source of fixed spectrum. (In our example this is a 130 kV peak X-ray spectrum from an X-ray tube.) The measurement parameters were optimized to produce a minimum relative error in the effective charge in the measurement, i.e., the error in Z divided by Z at an arbitrary point within the object. The measurement parameters to be optimized were chosen to be (1) the thickness of the filter, (2) the atomic number of the filter and (3) the relative time duration of the two measurements. This choice of the result to be optimized and the measurement parammeters chosen is reasonable; however, it is only one set out of a large number of possibilities which depend on the exact nature of the goals of the measurement and the apparatus used.

To illustrate the application of this technique, program 5 was generated, which performs a calculation for a particular set of conditions (e.g. a phantom of diameter 16 cm, etc.) For this particular case the minimum value for the relative statistical error in the measurement of the effective charge is 0.046594. It is obtained using a filter with an atomic number of 47.5 and a thickness of 0.0475 cm. The two measurements are to be performed for times (or beam intensities) in the ratio of 0.325 to 0.675.

X. DOSE CONSIDERATIONS H₂O BAG VS. SITAT

The relative density error is SITAT is $$\frac{\epsilon_D}{D} = -\frac{1}{2} \sqrt{\frac{\pi^2}{12Na^2}} \quad \frac{\epsilon_{T_1}}{T_1} \quad \frac{l}{\ln T_1} \qquad 103$$

To obtain this result two measurements are required. In equation 103 $T_1$ is the transmission, $l$ is the thickness, and the other symbols have been previously defined. For the case where an H₂O bag is employed to attentuate spectral artifacts, we define $T_{H_2O}$ as the transmission of water bag, $T$ the transmission of the object under observation, and $l'$ as the total thickness. The error is $$\frac{\epsilon_D}{D} = -\sqrt{\frac{\pi^2}{12Na^2}} \quad \frac{\epsilon_{T_{H_2O}} \cdot T}{T_{H_2O} \cdot T} \quad \frac{l'}{\ln(T_{H_2O} \cdot T)} \qquad 104$$

Assume we want equal error for the two techniques. Then equation 103 with $T_1 = T$ must equal equation 104, or:

$$\frac{1}{\sqrt{2}} \quad \frac{\epsilon_T}{T} \quad \frac{l}{\ln T} = \frac{\epsilon_{T_{H_2O}} \cdot T^{l'}}{T_{H_2O} \cdot T \ln (T_{H_2O} \cdot T)} \qquad 105$$

Using equation 56, the required incident intensities $I$ and $I_{BAG}$ are therefore $$\frac{1}{\sqrt{2}} \quad \frac{1}{\sqrt{IT}} \quad \frac{l}{\ln T} = \frac{1}{\sqrt{I_{BAG} T_{H_2O} \cdot T}} \quad \frac{l'}{\ln(T_{H_2O} \cdot T)} \qquad 106$$

OR $$\frac{I_{BAG}}{I} = \left(\frac{\ln T(l'/l)}{\ln(T_{H_2O} \cdot T)}\right)^2 \quad \frac{2}{T_{H2O}} =$$

$$\left[\frac{1}{1 + \ln T_{H_2O}/\ln T}\right]^2 \quad \frac{2}{T_{H_2O}} \left(\frac{l'}{l}\right)^2 \qquad 107$$

The relative dose indicated on the object is $$\frac{\text{DOSE BAG}}{\text{DOSE NO BAG}} = \frac{I_{BAG} \sqrt{T_{H_2O}}}{2I} = \qquad 108$$

$$\frac{1}{\sqrt{T_{H_2O}}} \left[\frac{1}{1 + \ln T_{H_2O}/\ln T}\right]^2 (\frac{l'}{l})^2$$

Note that when $T_{H_2O} = 1$ the two doses are equal. In equation 108 the two is introduced in the denominator to account for the fact that two measurements are required for SITAT. A square root of $T_{H_2O}$ is introduced in the numerator to account for dose attenuation by water in the incident beam.

We not consider eqn. 108. First note ln $(T_{H_2O} = \mu_H{_O} l$ AND ln $T \approx \mu l$ Thus $$\frac{\text{DOSE BAG}}{\text{DOSE NO BAG}} \approx 12 \frac{1}{\sqrt{T_{H_2O}}} \qquad 109$$

For water $$T_{H_2O} \approx e^{-3.34(\frac{l(cm)}{16})} \qquad (110)$$

Thus we find:

$$\frac{\text{DOSE BAG}}{\text{DOSE NO BAG}} = 1.67^{(\frac{l_{H_2O}(cm)}{16})} \qquad (111)$$

Using this result we obtain the following table:

| H₂O | Dose Bag/Dose No Bag |
|---|---|
| 0 cm | 1 |
| 5 | 1.685 |
| 10 | 2.84 |
| 15 | 4.78 |
| 20 | 8.06 |
| 25 | 13.6 |

From this table we see that a reduction of a factor of about three in dose is attained by using SITAT without a water bag as compared with a typical conventional, non-SITAT system using a water bag.

While the principles of the invention have now been made clear in the illustrated embodiments shown above, there will be obvious to those reasonably skilled in the art, many modifications in arrangement of components and choices of variables used in the practice of the invention. Without departing from the above enunciated principles, the appended claims are intended to cover and embrace any such modification within the limits only of the true spirit and scope of the invention.

What is claimed is:

1. A tomographic apparatus for graphically reproducing information from an object slice comprising:
   at least one source of penetrating radiation positioned to direct said radiation at the object;
   at least one detector responsive to radiation, each said detector positioned to receive said radiation after passage through the object for producing an output signal corresponding to said radiation at said detector;
   means coupled to said detector(s) for referencing said output signals to a series of test data derived from actual test measurements of objects having known attenuation characteristics, said referencing means producing intermediate signals, wherein said referencing means includes means to discriminate so that each of said facsimiles is representative of the distribution of a combination of atomic charge and electron density at each point within said object, wherein said combination is preselected based upon the application of an error function; and
   means for reconstructing said intermediate signals into at least two separate facsimiles, each of which is representative of a different distribution of the degree of attenuation within said object.

2. A tomographic apparatus for graphically reproducing information from an object slice comprising:
   at least one source of penetrating radiation positioned to direct said radiation at the object;
   at least one detector responsive to radiation, each said detector positioned to receive said radiation after passage through the object for producing an output signal corresponding to said radiation at said detector;
   means coupled to said detector(s) for referencing said output signals to a series of test data derived from actual test measurements of objects having known attenuation characteristics, said referencing means producing intermediate signals; and
   means for reconstructing said intermediate signals into at least two separate facsimiles, each of which is representative of a different distribution of the degree of attenuation within said object, wherein said reconstruction means comprises a non-reordering convolution and backprojection reconstructor.

3. A tomographic apparatus for graphically reproducing information from an object slice comprising:
   at least one source of penetrating radiation positioned to direct said radiation at the object;
   at least one detector responsive to radiation, each said detector positioned to receive said radiation after passage through the object for producing an output signal corresponding to said radiation at said detector;
   means coupled to said detector(s) for referencing said output signals to a series of test data derived from actual test measurements of objects having known attenuation characteristics, said referencing means producing intermediate signals; and
   means for reconstructing said intermediate signals into at least two separate facsimilies, each of which is representative of a different distribution of the degree of attenuation within said object;
   wherein error calculating means is coupled to said detector(s) and calculates the statistical error associated with said facsimiles as a function of the statistical errors associated with the detector measurements.

4. Apparatus as in claim 3 wherein said error calculating means further comprises means to determine the error associated with the use of a waterbag surrounding said object as a function of the statistical errors associated with the measurements made by said detector(s).

5. Apparatus as in claim 3 further comprising means for comparing said facsimile-associated statistical errors with a pre-calculated table of physical differences among a preselected set of typical items likely to be found within said object, said comprising means generating output data indicating which of said items can be distinguished using which of said facsimiles.

6. A method of removing spectral artifacts from tomograms of an unknown sample object, said tomograms produced by applying penetrating radiation from at least one source, detecting said radiation by at least one detector and producing output signals responsive thereto, said method comprising the steps of:
   performing a first set of test measurements with no object situated between said source(s) and said detector(s);
   performing at least one additional set of test measurements each with at least one test object of known attenuation characteristics situated between said source(s) and detector(s);
   converting said test measurements into a table linking detector output signals to radiation attenuation line integrals;
   performing two operational sets of measurements each with the unknown sample object situated between said source(s) and detector(s);
   transforming said operational measurements into two sets of operational line integrals by means of referencing said table; and reconstructing said operational line integrals into two output tomograms.

7. A method as in claim 6 wherein said radiation is X-radiation or gamma-radiation and emanates from said source in the shape of a fan lying in the same quasi-plane as said unknown sample object.

8. A method as in claim 6 wherein each of said output tomograms is representative of a combination of the atomic charge distribution and the electron density distribution within said unknown sample object.

9. A method as in claim 6 wherein said reconstructing step comprises the application of non-reordering convolution means to each of said sets of operational line integrals.

10. A method as in claim 6 wherein each of said tomograms accounts for distributions of photoelectric absorption, Compton scatter, and Rayleigh scatter within said unknown sample object.

11. A method as in claim 6 wherein said operational measurements step comprises taking two sets of measurements at two different peak energy settings of said source(s).

12. A method as in claim 11 wherein the level and duration of said energy settings are optimized.

13. A method as in claim 6 wherein each said detector(s) comprises two sub-detectors, each responsive to different photon energy ranges, wherein each sub-detector is simultaneously responsive to said radiation during said operational measurement step.

14. A method as in claim 13 wherein at least some of the physical characteristics of said subdetectors are optimized.

15. A method as in claim 6 wherein said operational measurement step comprises the substeps:
   taking a first operational group of measurements with a filter situated between said source(s) and said unknown sample object; and
   taking a second operational group of measurements with no filter.

16. A method as in claim 15 wherein physical attributes of said filter are optimized.

17. A method as in claim 16 wherein the physical attributes optimized include geometry of the filter, atomic number of the filter, and relative time duration for which the filter is employed.

* * * * *